United States Patent [19]

Staples

[11] Patent Number: 4,901,865

[45] Date of Patent: Feb. 20, 1990

[54] CAPSULE-INSPECTION APPARATUS

[75] Inventor: Stephen G. Staples, Indianapolis, Ind.

[73] Assignee: Eli Lilly and Company, Indianapolis, Ind.

[21] Appl. No.: 289,215

[22] Filed: Dec. 23, 1988

[51] Int. Cl.[4] .......................... B07C 7/04; B65B 67/00
[52] U.S. Cl. ...................................... 209/703; 53/390; 53/900; 209/936; 209/938; 414/675
[58] Field of Search ............... 209/509, 538, 546, 684, 209/702, 703, 707, 936, 938, 940, 942; 53/390, 900; 118/713; 414/675; 427/3, 444

[56] References Cited

U.S. PATENT DOCUMENTS

| | | | |
|---|---|---|---|
| 316,638 | 4/1885 | Moore | 53/390 X |
| 2,771,198 | 11/1956 | Danchig | 414/675 |
| 3,004,667 | 10/1961 | Hermelin | 209/705 X |
| 3,545,164 | 12/1970 | Middleton | 53/900 X |
| 3,709,698 | 1/1973 | Vandenberg et al. | 356/428 |
| 3,712,979 | 1/1973 | Padgitt | 362/296 |
| 3,757,943 | 9/1973 | Chae et al. | 209/551 |
| 3,838,766 | 10/1974 | Wagers, Jr. et al. | 198/380 |
| 4,123,352 | 10/1978 | Yamamoto et al. | 209/703 X |
| 4,144,970 | 3/1979 | McKnight et al. | 209/542 |
| 4,405,049 | 9/1983 | Deitz | 209/705 X |

Primary Examiner—Margaret A. Focarino
Assistant Examiner—Edward M. Wacyra
Attorney, Agent, or Firm—Barnes & Thornburg

[57] ABSTRACT

A capsule-inspection apparatus includes a base and a capsule-receiving tray slidable on the base to cause all of the capsules cradled in pockets formed in the tray to be turned simultaneously about their longitudinal axes to enhance visual inspection of substantially the entire exterior surface of the cradled capsules. An inspection mask is positionable on the tray to permit a user visually to inspect the coating dip line of coated caplets cradled in the tray quickly and easily to determine if the coating dip line is located substantially in the middle of the caplet to ensure that the caplet coating causes the caplet to resemble a two-piece capsule.

28 Claims, 2 Drawing Sheets

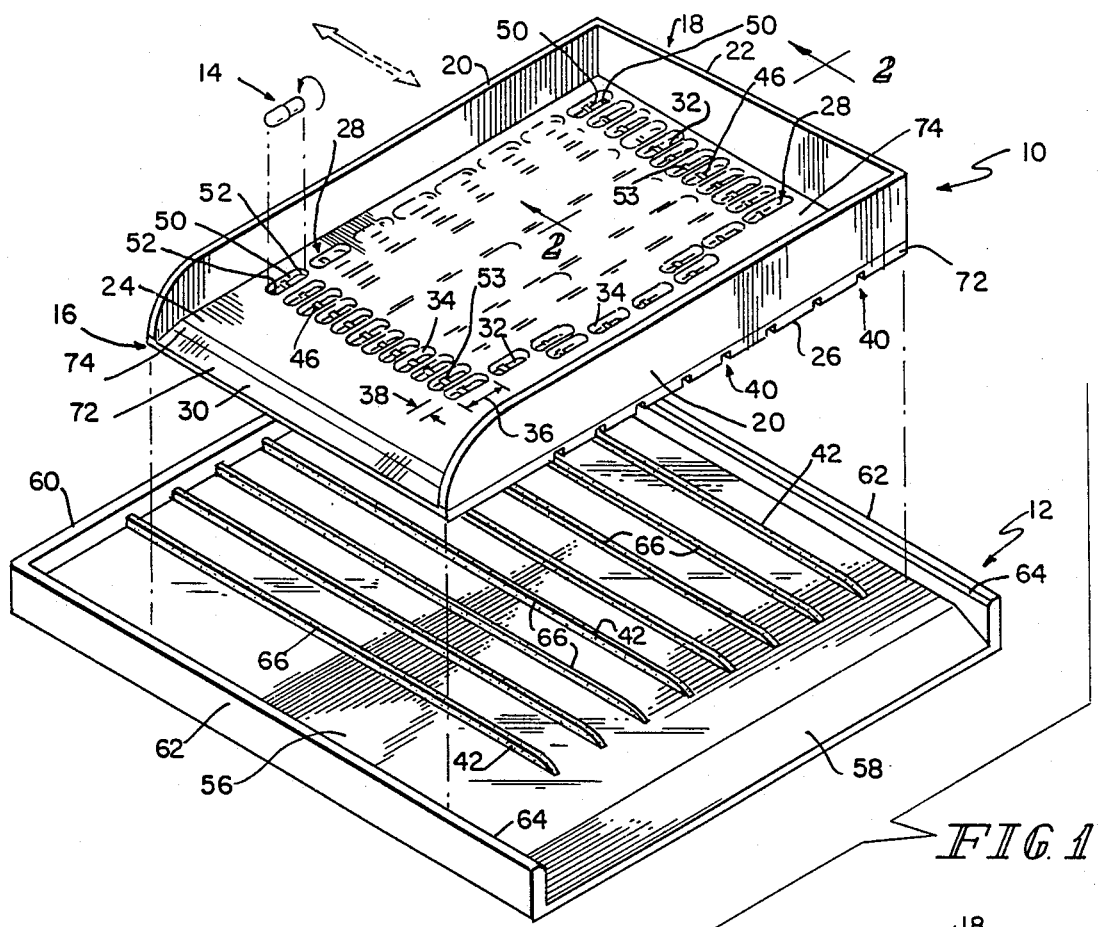
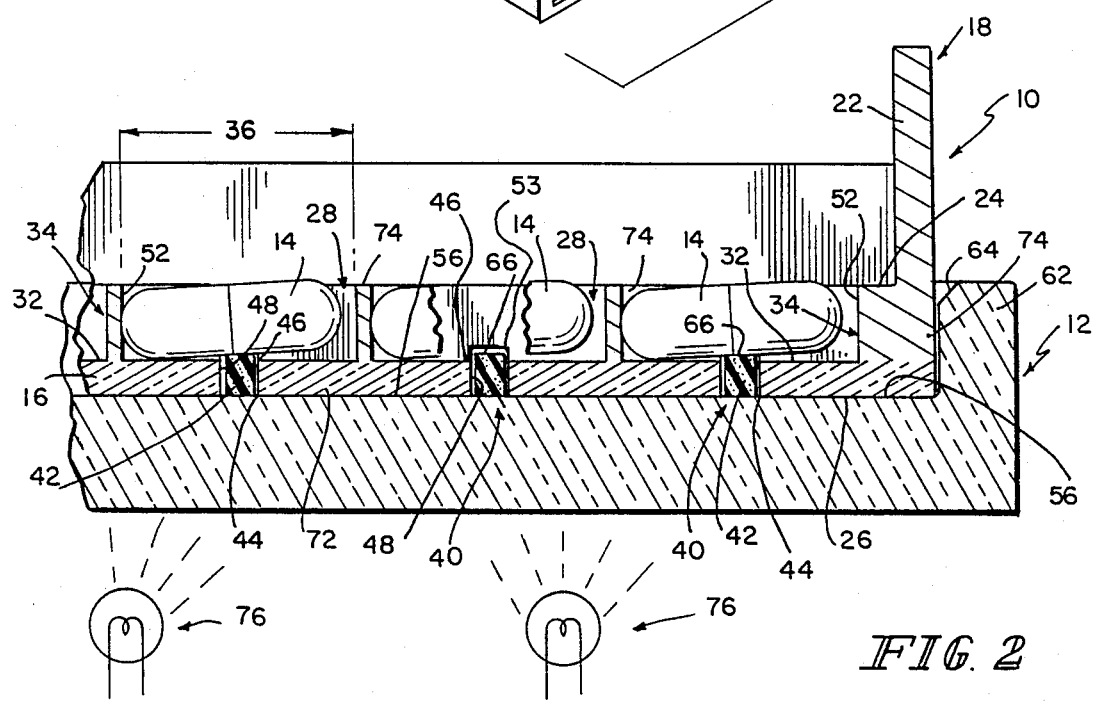

CAPSULE-INSPECTION APPARATUS

BACKGROUND AND SUMMARY OF THE INVENTION

The present invention relates to apparatus for handling capsules, caplets, and the like, and particularly to apparatus for enhancing visual inspection of the exterior of such capsules. More particularly, the present invention relates to apparatus for simultaneously turning each capsule in a collection of capsules to expose the exterior surface of each capsule to visual inspection and for inspecting a coating dip line of a caplet coated to resemble a capsule.

Specially configured paddles provided with empty receptacles are often used by pharmacists or other capsule handlers to simplify capsule counting prior to bottling. Typically, a handful of capsules is deposited onto the paddle and the paddle is shaken gently by the pharmacist to cause some of the capsules to fall into the paddle receptacles so that all receptacles are filled. The number of capsules remaining in these paddle receptacles after any excess capsules not captured in a receptacle have been removed from the paddle is equivalent to the number of receptacles provided in the paddle. In this way, the paddle is used to count a predetermined number of capsules. The number of capsules remaining in the paddle receptacles is then known and these capsules can then be removed from the paddle and put into bottles which are labeled and made ready for sale.

Those persons involved in dispensing or bottling capsules or caplets will recognize the need to inspect the exterior of each capsule or caplet visually to ensure that it conforms to a predetermined specification before it is distributed to a consumer. Typically, such inspection is a laborious and time-consuming process because of shortcomings in conventional capsule- or caplet-handling apparatus.

Capsules are inspected regularly to ensure that the top and bottom shells of each capsule mate correctly at the middle of the capsule. Such inspection can take place either before or after the capsules are filled with a powder or granule material.

Caplets are compressed or molded blocks of solid material (e.g., medicine) which are shaped to resemble capsules. Frequently, each end of a caplet is dipped into a selected coating material to form mating top and bottom shells thereon so that the outward appearance of the coated caplet looks exactly like a conventional two-piece capsule. It is important to caplet manufacturers that the coating "dip line" separating the top shell and the bottom shell is uniform and located substantially in the middle of the caplet to satisfy consumer demand for coated caplets that look like capsules. The location of the coating dip line of each caplet is typically examined during inspection of coated caplets to ensure that the coated top and bottom shells of each caplet resembles a conventional capsule shell in shape and size.

One object of the present invention is to provide an apparatus configured to cradle a certain number of capsules therein in such a way as to expose both outwardly facing and inwardly facing exterior surfaces of cradled capsules simultaneously while they are cradled in the apparatus to enhance inspectability and manipulability of the cradled capsules. That exterior portion of a capsule which faces inwardly toward the bottom of a receptacle in a conventional capsule-counting paddle in which it is received is typically hidden from view and inaccessible due to the configuration of the paddle and the paddle receptacles.

Another object of the present invention is to provide an apparatus in which all of the capsules cradled in pockets formed in a capsule-counting tray can be easily turned simultaneously about their longitudinal axes to enhance visual inspection of substantially the entire exterior surface of the cradled capsules.

Yet another object of the present invention is to provide an apparatus which is configured to permit a user visually to inspect the coating dip line of caplets cradled therein quickly and easily to determine if the coating dip line is located substantially in the middle of the caplet to ensure that the caplet coating causes the caplet to resemble a two-piece capsule.

According to the present invention, a capsule-inspection apparatus includes a plate member having top and bottom surfaces. The plate member is formed to include at least one pocket having a capsule-receiving opening in the top surface and a floor under the capsule-receiving opening for supporting a capsule disposed in the pocket. A passageway is also formed in the plate member for each pocket. Each passageway has an inlet opening in the bottom surface and an outlet opening in the floor to provide access to the pocket through the inlet opening in the bottom surface during inspection of a capsule disposed in the pocket.

In preferred embodiments, the plate member is formed to include an array of oblong capsule-receiving pockets arranged in a grid of rows and columns. A plurality of elongated grooves is formed in the plate member so that each groove has a longitudinally extending opening in the bottom surface. The grooves are aligned in spaced-apart parallel relation to position each groove underneath a companion one of the rows of capsule-receiving pockets in spaced-apart parallel relation thereto. Each groove formed in the plate member communicates with the passage inlet opening corresponding to each pocket in its companion row of pockets. Thus, it is possible to gain access to any pocket from a position underneath the plate member through the groove communicating with that pocket to permit a capsule disposed in a pocket to be rotated or ejected by an element disposed in the groove underlying the pocket.

The capsule-inspection apparatus further includes applying means movable relative to the plate member in said grooves for applying a rotation-inducing force to each capsule disposed in a pocket of the plate member to cause each such capsule to rotate about its longitudinal axis, thereby enhancing visual inspection of the exterior surface of the capsules received in the array of pockets. The applying means includes a base having a top surface for slidably receiving the plate member thereon and a plurality of spaced-apart parallel elongated ribs fixed to the top surface. The ribs are configured to slide in said grooves upon relative movement of the plate member and the base. Each rib includes means extending into the pockets for frictionally engaging capsules disposed in the pockets to rotate each such capsule about its longitudinal axis in response to sliding movement of the plate member on the top surface of the base.

The capsule-inspection apparatus is providable with an inspection mask formed to include aperture means for viewing a selected middle portion of each capsule disposed in a pocket upon placement of the inspection mask in a predetermined position above the top surface of the plate member. This feature is particularly well-suited for simultaneously inspecting the coating dip lines of a plurality of coated caplets disposed in the pockets of the plate member.

The inspection mask is formed to include an elongated aperture slot corresponding to each row of pockets in the array of pockets formed in the plate member. Locating means is provided on the plate member for locating the inspection mask in a predetermined position overlying the top surface of the plate member and the capsule-receiving openings formed therein to align each elongated aperture slot in vertically spaced-apart parallel relation to a selected row of pockets. Such alignment permits a user to view a selected middle portion of each coated caplet disposed in a pocket in the selected row of pockets through an elongated aperture slot formed in the inspection mask. The locating means includes an upstanding side wall coupled to the top surface of the plate member to define a border rim at least partially surrounding the array of capsule-receiving pockets and abutting the inspection mask to locate the inspection mask in its predetermined position.

It will be understood that the term "capsule" in the present application will be interpreted by those skilled in the art to mean capsule, caplet, pill, or other small package of two-piece construction or appearance.

Additional objects, features, and advantages of the invention will become apparent to those skilled in the art upon consideration of the following detailed description of the preferred embodiments exemplifying the best mode of carrying out the invention as presently perceived.

BRIEF DESCRIPTION OF THE DRAWINGS

The detailed description particularly refers to the accompanying figures in which:

FIG. 1 is a perspective assembly view of a preferred embodiment of a capsule-inspection apparatus in accordance with the present invention showing a capsule-receiving tray which is mountable on an underlying ribbed translucent base;

FIG. 2 is an enlarged side elevation view taken along lines 2—2 of FIG. 1 after placement of the tray on the ribbed transluscent base showing the insertion of the ribs into the capsule-receiving pockets in the tray to lift capsules disposed therein partially off the floor of the pocket, and the placement of illumination means underneath the translucent base;

DETAILED DESCRIPTION OF THE DRAWINGS

Figure 3:
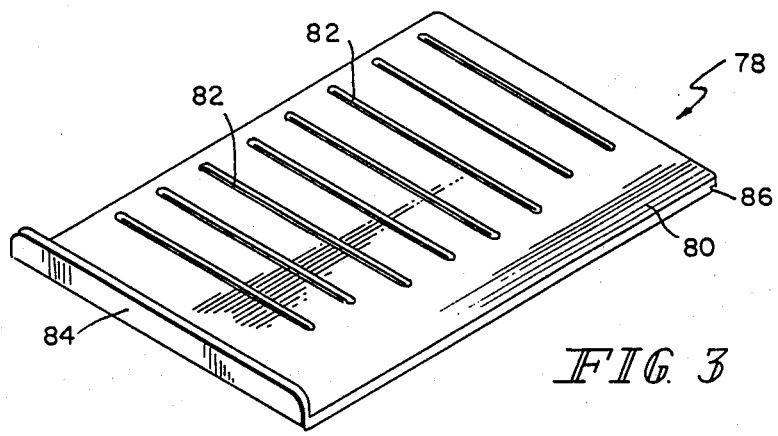
FIG. 3 is a perspective view of a preferred embodiment of a dip-line inspection mask in accordance with the present invention.

A capsule-receiving tray 10 is provided for use by a pharmacist or other capsule handler to simplify the task of counting and inspecting capsules prior to bottling. A base 12 is configured to support tray 10 for sliding movement thereon during inspection of capsules 14 received in tray 10. This apparatus 10, 12 can be used to count out a set number of capsules 14 in the tray 10 prior to bottling and also turn the capsules 14 about their longitudinal axes while the capsules 14 are still in the tray 10 during an inspection of the exterior surfaces of the capsules 14. The capsules 14 are turned by sliding the tray 10 back and forth on the base 12 in the manner described below. It will be appreciated that the capsules 14 can be turned one or more times at the discretion of the pharmacist simply by varying the number of times the tray 10 is reciprocated on the base 12.

Tray 10 includes a rectangular plate member 16 and an upstanding, U-shaped, capsule-retainer rim 18 coupled to the perimeter of plate member 16 as shown in FIG. 1. Capsule-retainer rim 18 includes a pair of spaced-apart parallel side walls 20 formed on plate member 16 during a molding operation and a back wall 22 joined to a U-shaped, vertically extending edge provided at the rear end of the tray by the plate member 16 and side walls 20. Preferably, the tray 10 is made of plastic.

Plate member 16 includes a top surface 24 as shown best in FIG. 1 and a bottom surface 26 as shown best in FIG. 2. Plate member 16 is formed to include an array of capsule-receiving pockets 28 arranged in a grid of rows extending between side walls 20 and columns extending between the beveled front end 30 of plate member 16 and back wall 22. Each pocket 28 has its primary opening in the top surface 24 of plate member 16 so that capsules 14 deposited onto top surface 24 are able to fall into the pockets 28 during a capsule counting operation. Front end 30 is beveled to enable a capsule handler to use tray 10 as a scoop to gather a plurality of capsules 14 on its top surface 24 from a bin (not shown) or other capsule stockpile.

Each pocket 28 illustratively has an oblong shape contoured to match the shape and size of capsules to be received therein and is defined by a capsule-support floor 32 and a continuous side wall 34 extending upwardly from floor 32 to meet with top surface 24 of plate member 16 as shown best in FIG. 2. The longitudinal dimension 36 of each pocket 28 is greater than its transverse dimension 38 as shown in FIG. 1 because of the oblong shape of the pockets 28. The pockets 28 are oriented so that their longitudinal dimensions 36 are aligned in parallel relation to the columns of pockets 28 extending along the length of tray 10 between the front and back ends 30, 22 of plate member 16.

A plurality of elongated grooves 40 are formed in the bottom surface 26 of plate member 16 to receive upstanding ribs 42 provided on the underlying base 12. The grooves 40 are arranged to lie in spaced-apart parallel relation to one another on the bottom of tray 10 and each groove 40 is situated to lie underneath one of the rows of pockets 28 extending across the width of tray 10 so that each groove 40 is matched with a companion row of capsule-receiving pockets 28.

As shown best in FIG. 2, each groove 40 in tray 10 includes an inlet opening 44 in the bottom surface 26 of plate member 16, an outlet opening 46 in the capsule-support floor 32 of each pocket 28 in its companion row of pockets, and a rib-receiving passageway 48 extending therebetween. Illustratively, each outlet opening 46 in floor 32 is defined by a rectangular slot extending between opposing flat side walls 50 provided by continuous pocket side wall 34 intermediate opposing curved end walls 52. Each flat side wall 50 includes an opening 53 communicating with outlet opening 46 in floor 32 as shown, for example, in FIG. 2 to admit a rib into the interior region of pocket 28 so that a top portion 66 of each rib 42 is above the level established by floor 32.

Base 12 includes a top face 56 for slidably supporting a tray 10 thereon and a plurality of spaced-apart parallel, upstanding ribs 42 thereon for engaging the downwardly-opening grooves 40 in the bottom of tray 10. The top face 56 includes a beveled tray ramp 58 at its front end and an upstanding end wall 60 at its rear end and a pair of spaced-apart parallel guide walls 62 extending between tray ramp 58 and end wall 60 as shown in FIG. 1. Each wall 62 is provided with an inwardly facing chamfered edge 64 as shown best in FIGS. 2 and 4.

Figure 4:
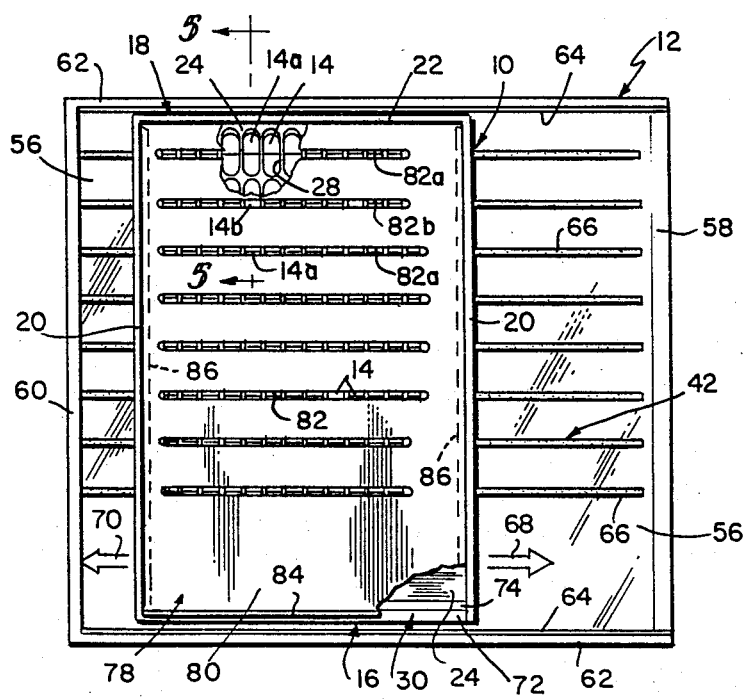
FIG. 4 is a top plan view of the capsule-inspection apparatus of FIGS. 1 and 2 showing placement of the dip-line inspection mask thereon during sliding movement of the capsule-receiving tray relative to the underlying ribbed base.

The top portion 66 of each rib 42 extends into the interior region of its companion pockets 28 because of openings 53 in pocket side walls 50 to lift at least a portion of any capsules 14 disposed therein off the pocket floor 32 as shown in FIGS. 2 and 4 upon placement of the bottom surface 26 of tray 10 on the top face 56 of base 12 to cause ribs 42 to engage grooves 40. The top portion 66 of each rib 42 includes a strip of friction material such as urethane resin arranged to contact any capsules 14 disposed in pockets 28.

In operation, tray 10 is conveniently used as a scoop to deposit an uncounted number of capsules on its top surface 24. Gentle side-to-side shaking of tray 10 will cause capsules 14 to fall into pockets 28 until all pockets 28 are filled. Excess capsules 14 are removed leaving a known number of capsules 14 in the tray pockets 28.

The capsule-laden tray 10 is then set down carefully onto the top face of the underlying base 12 so that the upstanding ribs 42 extend into the downwardly-opening grooves 40 formed in the tray. The friction strip on the top portion 66 of each rib 42 engages the capsules 14 disposed in the tray pockets 28 and lifts at least a portion of the capsules 14 off of the pocket floors 32 as shown in FIG. 2.

The tray 10 is slidable on the top face 56 of base 12 alternatively in a forward direction 68 toward tray ramp 58 and a rearward direction 70 toward end wall 60 as shown in FIG. 4 under the manual control of a pharmacist or other capsule handler using the apparatus. All capsules 14 cradled in the tray pockets 28 are rotated about their longitudinal axes in response to such relative movement of the tray 10 and base 12 because of frictional engagement between the stationary capsule-engaging friction strip on the top portion 66 of each rib 42 and the capsules 14 which are moved relative to the base 12 by the reciprocating tray 10. In effect, these friction strips 66 act to apply a rotation-inducing force to a capsule 14 disposed in each pocket 28 to permit each capsule 14 to be rotated or turned about its longitudinal axis while in its pocket 28. Advantageously, such capsule rotation enhances visual inspection of the exterior surface of each capsule 14 received in a tray pocket 28.

Figure 5:
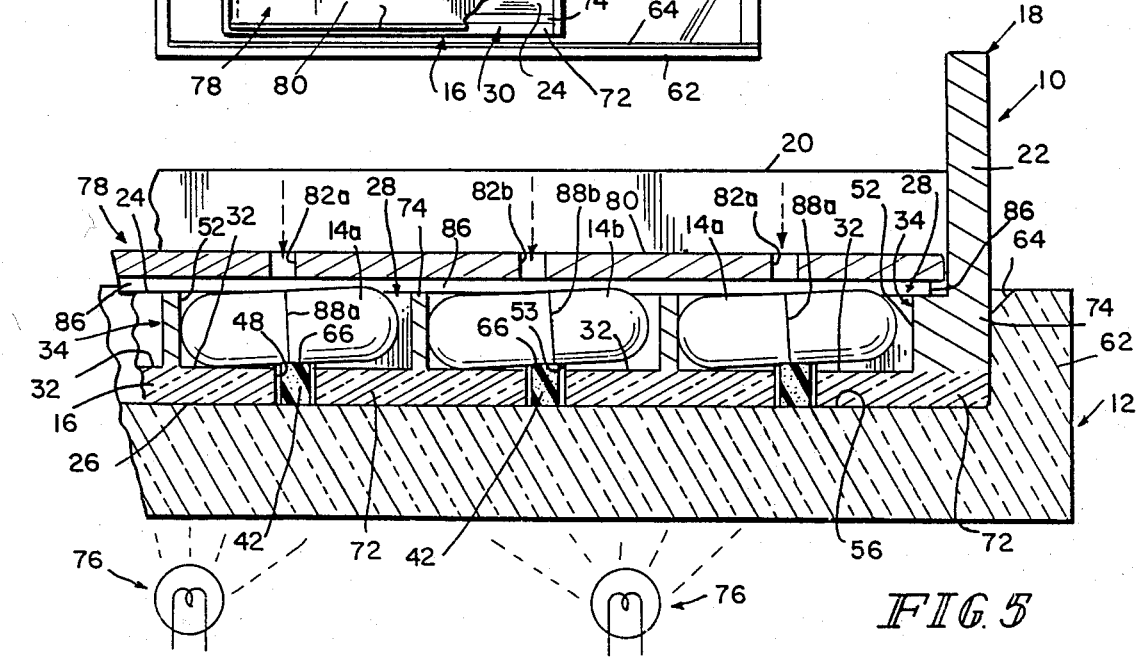
FIG. 5 is an enlarged side elevation view taken along lines 5—5 of FIG. 1 showing placement of viewing slots in inspection mask to permit visual inspection of the dip line of a coated caplet received in the underlying tray.

By moving a capsule-laden tray 10 back and forth in directions 68, 70 on base 12, it is possible for an observer to see substantially the entire exterior surface of each capsule 14 without removing any of the capsules 14 from the capsule-counting tray 10. Visibility of these capsules 14 is improved by making a bottom layer 72 of the tray 10 a light color such as white and a top layer 74 of the tray a relatively darker color such as black as shown in FIGS. 2 and 5. Further, the driving ribs 42 are opaque white to match the lower layer 72 of tray and base 12 is otherwise made out of a transparent or transluscent material to allow light from illumination means 76 at each inspection station to pass through base 10 to illuminate tray 10. In Particular, the contrast between the white pocket floors 32 and the black top surface 24 and pocket side wall 34 make the task of inspecting imprinted capsules 14 much easier, especially when inspection lights 76 are actuated to light up the white pocket floor 32 underneath each capsule 14.

An inspection mask 78 well-suited for use in inspecting the coating dip line of caplets coated to look like two-piece capsules is illustrated in FIG. 3. The inspection mask 78 is configured to be received in tray 10 during sliding movement of tray 10 with respect to base 12 so that a selected middle portion of each caplet 14 disposed in a tray pocket 28 can be viewed by an inspector while those caplets are being rotated about their longitudinal axes.

Inspection mask 78 includes a flat plate 80 formed to include a plurality of rows of aperture slots 82 arranged in spaced-apart parallel relation. A handle lip 84 is provided at the lower end of flat plate 80 and oriented to project upwardly from the top side of flat plate 80 as shown in FIG. 3. A shallow U-shaped ridge 86 is provided on the underside of flat plate 80 as shown in phantom lines in FIG. 4 (with the base of the U-shaped ridge hidden underneath the handle lip 84) to support a perimeter edge of inspection mask 78 on the top surface 24 of tray 10 so that aperture slots 82 lie over a middle region of companion rows of tray pockets 28 directly above the location where one would expect to see the coating dip line of a properly coated caplet disposed in the tray pockets 28.

In operation, the inspection mask 78 is placed over the array of capsule-receiving pockets 28 in plate member 16 and nested inside the U-shaped capsule-retainer rim 18 of tray 10 to locate in the predetermined position illustrated in FIGS. 4 and 5 above the top surface 24 of the plate member 16. A user need only look through the aperture slots 82 as the tray 10 is reciprocating in directions 68, 70 on base 12 to examine the location of the coating dip line as caplets 14 are rotating about their longitudinal axes of the tray pockets 28 covered by inspection mask 78. For example, referring to FIG. 5, the coating dip line 88a of caplets 14a is properly located and therefore visible to an observer through aperture slots 82a whereas the coating dip line 88b of caplet 14b is hidden from view underneath the flat plate 80 of inspection mask 78 indicating that the coating on caplet 14b is defective because the dip line is not properly located in the middle of the caplet 14b.

Although the invention has been described in detail with reference to certain preferred embodiments, variations and modifications exist within the scope and spirit of the invention as described and defined in the following claims.

What is claimed is:

1. A capsule-inspection apparatus comprising
a plate member having top and bottom surfaces, the plate member being formed to include at least one pocket having a capsule-receiving opening in the top surface and a floor under the capsule-receiving opening for supporting a capsule disposed in the pocket and a passageway for each pocket having an inlet opening in the bottom surface and an outlet opening in the floor to provide access to the pocket through the inlet opening in the bottom surface during inspection of a capsule disposed in the pocket.

2. The apparatus of claim 1, further comprising applying means insertable into the at least one pocket through the passageway for applying a rotation-inducing force to a capsule disposed in each pocket to permit each capsule to be rotated while in its pocket, thereby enhancing visual inspection of the exterior surface of each capsule received in the plate member.

3. The apparatus of claim 1, wherein the plate member is formed to include at least one row of pockets, an elongated groove for each row of pockets, each elongated groove providing a strip-receiving opening in the back surface of the plate member and communicating with the passageway inlet opening of each pocket in its companion row of pockets, and further comprising a base including a plurality of friction strips, each friction strip being configured to fit into a companion elongated groove formed in the plate member and extend into each pocket in the row of pockets associated with said elongated groove through the outlet opening in the floor to apply a rotation-inducing force to each capsule disposed in a pocket in said row of pockets upon relative movement of the base and the plate member.

4. The apparatus of claim 1, wherein the plate member is formed to include an array of capsule-receiving pockets arranged in a grid of rows and columns and a plurality of elongated grooves having longitudinally extending openings in the bottom surface, the grooves being aligned in spaced-apart parallel relation to position each groove underneath a companion one of the rows of capsule-receiving pockets in spaced-apart parallel relation thereto so that each groove formed in the plate member communicates with the passage inlet opening corresponding to each pocket in its companion row of pockets.

5. The apparatus of claim 4, wherein each pocket has an oblong shape causing its longitudinal dimension to be greater than its transverse dimension and is oriented to align its longitudinal dimension in parallel relation to the pocket columns formed in the plate member and the outlet opening in the floor of each pocket is configured to provide an elongated rectangular slot extending along the transverse dimension of the pocket to communicate with its underlying companion groove.

6. The apparatus of claim 4, further comprising applying means movable in said grooves relative to the plate member for applying a rotation-inducing force to each capsule disposed in a pocket of the plate member to cause each such capsule to rotate about its longitudinal axis, thereby enhancing visual inspection of the exterior surface of the capsules received in the array of pockets.

7. The apparatus of claim 6, wherein the applying means includes a base having a top surface for slidably receiving the plate member thereon and a plurality of spaced-apart elongated ribs fixed to the top surface and configured to slide in said grooves upon relative movement of the plate member and the base, and each rib includes means for frictionally engaging capsules disposed in the pockets to rotate each such capsule about its longitudinal axis in response to sliding movement of the plate member on the top surface of the base.

8. The apparatus of claim 1, further comprising an inspection mask formed to include aperture means for viewing a selected middle portion of each capsule disposed in a pocket upon placement of the inspection mask in a predetermined position above the top surface of the plate member.

9. The apparatus of claim 1, wherein the plate member is formed to include at least one row of pockets, and further comprising an inspection mask formed to include at least one elongated aperture slot and locating means on the plate member for locating the inspection mask in a predetermined position overlying the top surface of the plate member and the capsule-receiving openings formed therein to align each elongated aperture slot in vertically spaced-apart parallel relation to a selected row of pockets to permit a user to view a selected middle portion of each capsule disposed in a pocket in the selected row of pockets through an elongated aperture slot formed in the inspection mask.

10. The apparatus of claim 9, wherein the plate member is formed to include an array of capsule-receiving pockets and the locating means includes an upstanding side wall coupled to the top surface of the plate member to define a border rim at least partially surrounding the array of capsule-receiving pockets and abutting the inspection mask to locate the inspection mask in its predetermined position so that a user is able to view the selected middle portion of each capsule disposed in a pocket in the array of pockets through the at least one aperture slot.

11. The apparatus of claim 1, wherein the plate member includes an interior side wall in each capsule-receiving pocket, the interior side wall of each pocket is configured to surround a capsule disposed in the pocket and interconnect the top surface of the plate member and the floor of the pocket, and the floor of each pocket is provided with a light color selected to contrast with a relatively darker color provided on at least one of the top surfaces of the plate member and the interior side wall of each pocket to enhance visual inspection of capsules disposed in the pockets.

12. The apparatus of claim 11, wherein said light color is white and said relatively darker color is black.

13. A capsule-inspection apparatus comprising
a base having a top surface and a plurality of spaced-apart parallel elongated ribs fixed to the top surface, and
a tray formed to include a plurality of spaced-apart parallel, downwardly opening grooves aligned to receive the elongated ribs therein upon placement of the tray on the top surface of the base, a plurality of rows of upwardly opening, capsule-receiving pockets, each row of upwardly opening pockets being oriented to lie above one of the downwardly opening grooves and extend in parallel alignment therewith, and admitting means interconnecting each pocket and its companion groove for admitting one of the ribs fixed to the tray into the pocket upon placement of the tray on the top surface of the base to insert each rib in its companion groove so that each rib frictionally engages a capsule disposed in a capsule-receiving pocket formed in the tray to rotate the capsule about its longitudinal axis relative to the tray upon sliding movement of the tray on the top surface of the base.

14. The apparatus of claim 13, wherein the tray further includes a floor in each pocket for supporting a capsule disposed in the pocket and the floor is formed to include the admitting means.

15. The apparatus of claim 14, wherein the tray further includes a top face formed to define capsule-receiving openings into the pockets and an interior side wall in each pocket configured to surround a capsule disposed in the pocket and interconnect the top face of the tray and the floor of the pocket, and the side wall in each pocket is formed to include a pair of opposing rib-receiving openings situated to lie on opposite sides of a capsule supported on the floor intermediate the floor and the capsule-receiving opening and to communicate with the admitting means in the floor so that a capsule-engaging surface of each rib is situated above the floor of the pocket upon reception of the base ribs in the tray grooves to lift at least a portion of a capsule disposed in the pocket off the pocket floor, thereby enhancing rotatability of capsules disposed in the tray pockets.

16. The apparatus of claim 15, wherein the floor of each pocket is provided within a light color selected to contrast with a relatively darker color provided on at least one of the top face of the tray and the interior side wall of each pocket to enhance visual inspection of capsules disposed in the tray pockets.

17. The apparatus of claim 15, wherein the interior side wall of each pocket includes a pair of opposing elongated flat portions and a pair of opposing curved portions, the flat portions and curved portions are arranged in alternating sequence to provide each pocket with an oblong shape, the elongated flat portions are situated in spaced-apart parallel relation to position the admitting means therebetween, and each of the elongated flat portions is formed to include one of the rib-receiving openings.

18. The apparatus of claim 13, further comprising an inspection mask formed to include aperture means for viewing a selected middle portion of each capsule disposed in a tray pocket upon placement of the inspection mask in a predetermined position on the tray.

19. The apparatus of claim 18, wherein the inspection mask is formed to include a plurality of rows of elongated aperture slots arranged to confront the plurality of rows of upwardly opening, capsule-receiving pockets in opposing relation cooperatively to define said aperture means.

20. The apparatus of claim 18, wherein the tray further includes means for locating the inspection mask in its predetermined position so that the aperture means overlies the upwardly opening, capsule-receiving pockets to permit a user visually to inspect the selected middle portion of each capsule received in a tray pocket.

21. A capsule-inspection apparatus comprising
a tray formed to include a plurality of upwardly opening, capsule-receiving pockets aligned in rows to form an array and a downwardly opening, elongated groove under each row of pockets, each pocket including a floor for supporting a capsule disposed therein, the floor being formed to include an aperture opening into the underlying groove, and
a base having a tray-receiving surface and a plurality of upstanding ribs arranged to engage the downwardly opening grooves in slidable mating relation upon placement of the tray on the tray-receiving surface of the base, each rib including an upwardly facing friction surface extending into the pockets of its companion groove via the floor apertures in said pockets to frictionally engage a capsule disposed therein so that each engaged capsule is rotated about its longitudinal axis by the friction surface in response to sliding movement of the tray on the tray-receiving surface of the base.

22. The apparatus of claim 21, wherein the tray further includes a top face formed to define capsule-receiving openings into the pockets and an interior side wall in each pocket configured to surround a capsule disposed in the pocket and interconnect the top face of the tray and the floor of the pocket, and the side wall in each pocket is formed to include a pair of opposing rib-receiving openings situated to lie on opposite sides of a capsule supported on the floor intermediate the floor and the capsule-receiving opening and communicate with apertures in the floor so that a capsule-engaging surface of each rib is situated above the floor of the pocket upon reception of the base ribs in the tray grooves to lift at least a portion of a capsule disposed in the pocket off the pocket floor, thereby enhancing rotatability of capsules disposed in the tray pockets.

23. The apparatus of claim 22, wherein the floor of each pocket is provided with a light color selected to contrast with a relatively darker color provided on at least one of the top face of the tray and the interior side wall of each pocket to enhance visual inspection of capsules disposed in the tray pockets.

24. The apparatus of claim 21, wherein the plate member includes an interior side wall in each capsule-receiving pocket, the interior side wall of each pocket is configured to surround a capsule disposed in the pocket and interconnect the top surface of the plate member and the floor of the pocket, and the floor of each pocket is provided with a light color selected to contrast with a relatively darker color provided on at least one of the top surface of the plate member and the interior side wall of each pocket to enhance visual inspection of capsules disposed in the pockets.

25. The apparatus of claim 24, wherein said light color is white and said relatively darker color is black.

26. The apparatus of claim 21, further comprising an inspection mask formed to include aperture means for viewing a selected middle portion of each capsule disposed in a tray pocket upon placement of the inspection mask in a predetermined position on the tray.

27. The apparatus of claim 26, wherein the inspection mask is formed to include a plurality of rows of elongated aperture slots arranges to confront the plurality of rows of upwardly opening, capsule-receiving pockets in opposing relation cooperatively to define said aperture means.

28. The apparatus of claim 26, wherein the tray further includes means for locating the inspection mask in its predetermined position so that the aperture means overlies the upwardly opening, capsule-receiving pockets to permit a user visually to inspect the selected middle portion of each capsule received in a tray pocket.

* * * * *